US009892505B2

(12) United States Patent
Redtel (10) Patent No.: US 9,892,505 B2
(45) Date of Patent: Feb. 13, 2018

(54) METHOD AND DEVICE FOR DETERMINING VITAL PARAMETERS

(71) Applicant: Kenkou GmbH, Bochum (DE)

(72) Inventor: Holger Redtel, Perleberg (DE)

(73) Assignee: Kenkou GmbH, Bochum (DE)

( * ) Notice: Subject to any disclaimer, the term of this patent is extended or adjusted under 35 U.S.C. 154(b) by 0 days.

(21) Appl. No.: 14/441,917

(22) PCT Filed: Nov. 8, 2013

(86) PCT No.: PCT/EP2013/073362
§ 371 (c)(1),
(2) Date: May 11, 2015

(87) PCT Pub. No.: WO2014/072461
PCT Pub. Date: May 15, 2014

(65) Prior Publication Data
US 2015/0287187 A1 Oct. 8, 2015

(30) Foreign Application Priority Data

Nov. 11, 2012 (DE) .................. 10 2012 021 940
Jan. 30, 2013 (DE) .................. 10 2013 001 553
(Continued)

(51) Int. Cl.
*G06K 9/00* (2006.01)
*G06T 7/00* (2017.01)
(Continued)

(52) U.S. Cl.
CPC .......... *G06T 7/0012* (2013.01); *A61B 5/0077* (2013.01); *A61B 5/021* (2013.01);
(Continued)

(58) Field of Classification Search
CPC ........................ G06T 7/0012; A61B 5/6898
See application file for complete search history.

(56) References Cited

U.S. PATENT DOCUMENTS 5,954,583 A 9/1999 Green
6,200,270 B1 3/2001 Biehl et al.
(Continued)

FOREIGN PATENT DOCUMENTS

DE 196 48 935 A1 5/1998
DE 10 2008 042 115 A1 3/2010
(Continued)

OTHER PUBLICATIONS

Hao-Yu Wu et al., "Eulerian Video Magnification for Revealing Subtle Changes in the World", ACM Transactions on Graphics, vol. 31, No. 4, Article 65, Jul. 2012, XP055124867, ISSN:0730-0301, DOI: 10.1145/2185520.2185561.
(Continued)

*Primary Examiner* — Oneal R Mistry
(74) *Attorney, Agent, or Firm* — Collard & Roe, P.C.

(57) ABSTRACT

The Invention relates to a method for determining vital parameters of a human body by means of a device (10) with at least one optical recording unit (11) and a computinig unit (12), said method comprising the following steps: recording a sequence of Individual image data of a single limited area of the skin (30) of the human body by means of the optical recording unit (11); evaluating the image data, including determining a pulse wave transit time; and determining vital parameters of the human body from the image data by means of the computing unit (12). The invention further relates to a method for authenticating a person and to a method for identifying a reaction of a person.

27 Claims, 3 Drawing Sheets

(30) Foreign Application Priority Data

Apr. 4, 2013 (DE) .................. 10 2013 005 610
May 20, 2013 (DE) .................. 10 2013 008 442

(51) Int. Cl.
*A61B 5/0205* (2006.01)
*A61B 5/021* (2006.01)
*G06T 7/20* (2017.01)
*H04N 5/225* (2006.01)
*A61B 5/00* (2006.01)

(52) U.S. Cl.
CPC ........ *A61B 5/0205* (2013.01); *A61B 5/02125* (2013.01); *G06K 9/00892* (2013.01); *G06T 7/0016* (2013.01); *G06T 7/20* (2013.01); *H04N 5/2256* (2013.01); *A61B 5/6898* (2013.01); *A61B 2562/0204* (2013.01); *A61B 2562/0219* (2013.01); *G06T 2200/04* (2013.01); *G06T 2207/10012* (2013.01); *G06T 2207/10024* (2013.01); *G06T 2207/20021* (2013.01); *G06T 2207/30076* (2013.01); *G06T 2207/30088* (2013.01)

(56) References Cited

U.S. PATENT DOCUMENTS

| | | | |
|---|---|---|---|
| 6,621,917 B1 | 9/2003 | Vilser | |
| 8,303,807 B2 | 11/2012 | Zhang | |
| 2008/0045847 A1 | 2/2008 | Farag et al. | |
| 2009/0203972 A1 | 8/2009 | Heneghan et al. | |
| 2011/0054310 A1* | 3/2011 | Taylor | A61B 5/0059 600/425 |
| 2012/0195469 A1* | 8/2012 | Kirenko | G06T 7/20 382/103 |
| 2013/0226007 A1* | 8/2013 | Jeanne | A61B 6/5288 600/473 |
| 2013/0322729 A1 | 12/2013 | Mestha et al. | |
| 2014/0073969 A1* | 3/2014 | Zou | A61B 5/02108 600/479 |
| 2014/0107493 A1* | 4/2014 | Yuen | H04W 4/027 600/473 |
| 2014/0205165 A1* | 7/2014 | Jeanne | A61B 5/117 382/128 |
| 2015/0182132 A1* | 7/2015 | Harris | A61B 5/0295 340/870.01 |
| 2015/0193650 A1* | 7/2015 | Ho | A61M 16/06 382/128 |
| 2015/0297142 A1* | 10/2015 | De Jaam | G06K 9/00503 600/407 |

FOREIGN PATENT DOCUMENTS

| | | |
|---|---|---|
| EP | 2 000 084 A1 | 12/2008 |
| EP | 2 631 874 A1 | 8/2013 |
| JP | 2001 338295 A | 12/2001 |
| KR | 2011 0003163 A | 1/2011 |
| WO | 97/17016 A2 | 5/1997 |
| WO | 2007/101431 A1 | 9/2007 |

OTHER PUBLICATIONS

Macková, Hana, "Pulse Wave Velocity in Arteries", Sep. 12, 2012, XP008184082, URL: https://dspace.cvut.cz/handle/10467/13174.

* cited by examiner

METHOD AND DEVICE FOR DETERMINING VITAL PARAMETERS

CROSS REFERENCE TO RELATED APPLICATIONS

This application is the National Stage of PCT/EP2013/073362 filed on Nov. 8, 2013, which claims priority under 35 U.S.C. § 119 of German Application Nos. 10 2012 021 940.7 filed on Nov. 11, 2012, 10 2013 001 553.7 filed on Jan. 30, 2013, 10 2013 005 610.1 filed on Apr. 4, 2013, and 10 2013 008 442.3 filed on May 20, 2013, the disclosures of which are incorporated by reference. The international application under PCT article 21(2) was not published in English.

BACKGROUND OF THE INVENTION

1. Field of the Invention

The invention relates to a method for determining vital parameters of a human body by means of a device, in particular a smart device. The invention further relates to a device for determining vital parameters of a human body, a method for authenticating a person, and a method for identifying a reaction of a person.

The determination of vital parameters such as for example pulse, blood pressure, breathing frequency, oxygen saturation, pulse wave variability, and blood glucose is more and more widely spread in everyday life and utilized not only for medical purposes. Formerly, these parameters were merely utilized for a so-called patient curve, for example at a hospital or in competitive sports. It served for monitoring a patient before and after a treatment in order to exactly document its state of health and to record any improvement or deterioration in this state of health, respectively.

In competitive sports, vital parameters are utilized to document the performance efficiency of an athlete and to ascertain the success of training. Accordingly, vital parameters are utilized to find out whether the training or diet of an athlete needs to be changed.

More recently, vital parameters have become interesting and important for domestic diagnosis and leisure sports, too. For example, patients are not necessarily subjected any longer to stationary treatment at a hospital, but frequently treated ambulantly on an outpatient basis, with aftercare taking place at home. For example, after a treatment, a patient has to record its own pulse.

2. The Prior Art

To this end, a device is frequently utilized that is comprised of a chest strap with sensors and a recording unit. The sensors of the chest strap record the pulse beats directly on the patient's chest. The data are then transmitted to the recording unit. The recording unit is capable of storing the data over several hours and even days, for example for a long-term cardiogram. The data are then read-out and evaluated, for example, by medical staff.

The device, however, is uncomfortable for a patient to wear, because the chest strap, for example, has to be worn uninterruptedly for a long-term cardiogram. This restricts the patient's mobility and moreover, it is obstructive in patient's day-to-day washing. Additionally, the patient has to constantly carry the recording device with him/her.

The situation with long-term blood glucose measurements is similar, in which a blood pressure cuff needs to be worn by a patient, for example for 24 hours, applying pressure to the blood pressure cuff every 15 minutes, for example.

Another example for a vital parameter frequently measured at home is blood glucose. Diabetics are often bound to determine their blood sugar before and after each meal. Thereby, a patient may decide whether a self-medication with insulin is necessary. In most cases, an appliance is utilized which comprises a needle, a measuring strip, and an evaluation unit. The patient pierces the needle, for example, into a finger pad to tap a drop of blood. By the aid of the measuring strip, the blood is then transferred to the evaluating unit, and the blood sugar is determined. While this procedure is cumbersome and inconvenient, it is also painful for the patient.

In leisure sports, it is common practice to monitor the pulse during the training and to control the training via the pulse. A runner can objectively monitor the intensity of his/her training via his/her pulse. Similar to the medical field, chest straps with sensors are frequently utilized which for example transmit the signals to a sports watch or an audio device for evaluation. The chest strap is fastened with high compression to the athlete's chest in order to prevent its slippage during the training. Thereby, the chest strap noticeably restricts the athlete's mobility and due to high compression, it is inconvenient to wear.

From prior art in technology, it is furthermore known to determine vital parameters from the pulse wave transit time and, possibly, in combination with pulse frequency (RR-interval). Pulse wave transit time is a cardiovascular measuring value. It describes the time needed by a pulse wave to cover a certain distance in the vascular system of a human body. By measuring the pulse wave transit time, conclusions can be drawn as to significant vital parameters such as blood pressure as well as elasticity of vessels. The most frequent configuration is measuring the pulse wave transit time from the heart to a finger. This always requires in particular a measurement on at least two measuring points. The beginning of the pulse wave, i.e. the point of time of the heart contraction, can be determined by means of an electrocardiogram (ECG). To this end, the ECG maximum, the so-called R-indent or R-wave, is utilized. At the finger, the signal can be detected photoplethysmographically by means of a pulse oximeter. Studies have shown that at least over short periods of time the pulse wave transit time can be utilized for determining blood pressure. It may however still require a reference measurement.

The determination of the pulse wave transit time and vital parameters thereof is known, for example, from printed publications WO 97/17016, EP 0 859 569, DE 10 2008 042 115 and WO 2007/101431.

Prior art in technology steadily has a disadvantage in that the devices and methods cannot or cannot be used practically in day-to-day life, because they require professional medical knowledge or because they are to be handled in a technically complicated manner. Moreover, as has already been pointed out above, a reference measurement of the pulse wave transit time is needed in most cases which also complicates its practical application in the medical field, for example at a hospital or in competitive sports.

SUMMARY OF THE INVENTION

Against this background, it is the object of the present invention to provide a method and a device that allow for a simple and cost-effective determination of vital parameters.

The present invention achieves this object by a method described herein, a device described herein, and further by a method described herein.

In particular, the present invention relates to a method, comprising the following steps:
   recording a sequence of individual image data of a limited area of the skin of the human body by means of the optical recording unit;
   evaluating the image data, including determining a pulse wave transit time; and
   determining vital parameters of the human body from the image data by means of the computing unit.

With particular advantage as opposed to prior art in technology, recording of the sequence of image data is carried out by means of a device, in particular a smart device, comprising at least one optical recording unit and one computing unit (also to be designated as a data processing unit). Accordingly, the device may be, for example, a cell phone, also called smart phone. As is well known, smartphones are compact computers with the usual architecture comprised of CPU, RAM, ROM, and data bus, with an integrated video recording hardware (digital camera), display, as well as input/output and communication interfaces. Other exemplary devices are watches, glasses, or other apparel, also called intelligent apparel) provided with a computing unit. These appliances or devices are mostly carried by a user with him/her already for other purposes, for example to use them for making phone calls or downloading information from the internet. Thus, the method can be carried out in an advantageous manner with a device already existing.

Another advantage results in that in contrast with prior art in technology, only one measuring location, i.e. a single limited coherent area of the skin of the human body is necessary. In principle, any arbitrary spot of the skin can be utilized. It is however advantageous to utilize a spot well circulated with blood, because the image data in this way are more informative and have a more favorable signal-to-noise ratio.

The sequence of individual image data may be a video sequence or mere individual images in a temporal sequence. A video sequence contains more information that can be evaluated, and thus it improves the result of the determination of vital parameters, increasing the accuracy in particular. Individual images are simpler to save, which is of advantage in particular with a limited storage space in a working memory of the computing unit. Individual images moreover increase the speed in determining vital parameters, because less information has to be evaluated.

Pulse wave transit time is determined from the image data, that means by evaluating them. For example, this can be accomplished by identifying the pulse wave passing through the area of the skin as well as by an associated temporal measurement of the pulse wave velocity. The measurement can be taken, for example, in an interval from one R-wave to the next R-wave, also called RR-interval. The vital parameters can then be determined from the pulse wave transit time determined this way. Pulse wave transit time and pulse wave velocity furnish information on the vascular situation. Rigid vessels with restricted vasomotricity lead to different transit times and velocities of the pulse wave. Consequently, conclusions as to the status of a vessel wall can be drawn by inferring to the transit time and velocity of the pulse wave. Based on these parameters, it is possible to diagnose an arteriosclerotic change of the vessels at a very early stage and to prevent progression of arteriosclerosis by implementing appropriate changes to lifestyle (e.g. nutrition poor in fat and sodium, sports activities).

It should be mentioned that the image data of the area of the skin of a human body need not mandatorily be acquired directly by means of the optical recording unit. It is also possible to record a pictorial reproduction, for example a television picture, of the area of the skin in order to perform the determination of vital parameters in accordance with the present invention. In this manner, for example, vital parameters of a person reflected on a television monitor can be determined in accordance with the present invention.

Examples for application of the method are the measurement of blood pressure in monitoring of persons, blood pressure measurement on the skin, blood pressure measurement and monitoring in sleep laboratories, blood pressure measurement in performance diagnostics, blood pressure measurement as a permanent measurement, for example over several hours or days, control of velocities for blood discharge or blood intake, blood purification such as for example dialysis, thrombocytes, plasma. Blood pressure is regarded as one of the medical standards in evaluating the cardiovascular situation at rest and under physical stress. The physiological limit values at rest and under stress are extensively described and stipulated in guidelines. A continuous determination of the blood pressure under stress, however, is currently not possible, because the blood pressure can be determined by means of blood pressure cuffs only at predefined points of time. It is only by way of the present invention that a continuous measurement becomes possible. Inventively the blood pressure is determined from the velocity of the pulse wave/pulse wave transit time; a short transit time from the heart to the finger is indicative for a high blood pressure, because the vessels are positioned narrowly. When applying the present invention to blood pressure measurement, a calibration is preferably made at rest and under stress. Afterwards, the blood pressure can be measured continuously. The inventive method can be implemented in all groups of persons; owing to the non-invasive measurement, everybody can take the measurement without any risk. A blood pressure determination over an extended period of time becomes possible not only for healthy athletes, but also for risk groups, e.g. heart patients and pregnant women. Users are afforded a possibility to identify blood pressure peaks and situations that lead to a rise. Thereof, it consequently results that users can avoid relevant situations and learn to better control their blood pressure by making changes to their lifestyle.

In a particular advantageous embodiment, the determination of the pulse wave transit time comprises the following steps:
   subdividing into tiles the area of the skin reflected in the individual image data;
   determining a color, brightness and/or volume in each of the tiles of the individual image data;
   comparing the color, brightness and/or volume of the tiles in the consecutive image data of the sequence;
   determining a modification profile of the color, brightness and/or volume of each tile in accordance with the sequence of image data, wherein the modification profile reflects a pulse wave propagating through the area of the skin; and
   computing the pulse wave transit time from the modification profile.

Subdividing the image data into tiles, also called grids, can be accomplished in variable accuracy. For example, this depends on the size of the area of the skin from which image data are recorded. With a large area, the subdivision into tiles can be made in less detail. With a small area, a plurality of tiles is used. For example, the image data per single image are subdivided into 100 times 100 tiles, whereby distances on the skin for determination of the pulse wave transit time can be determined accordingly precisely. For each tile of an individual image, the color, brightness and/or volume are determined. Thereby, with the sequence of image data, one obtains the sequence of color, brightness, and/or volume of each tile. In a next step, the individual images are compared with each other in order to be able to ascertain a change in color, brightness and/or volume. From the changes in color, brightness and/or volume of the tiles, a modification profile, i.e. a temporal sequence of changes, is then established. Thereby, it is possible to determine the pulse wave and its propagation through the area of the skin. The pulse wave transit time is then determined from this modification profile. To this end, one may take recourse to assumptions, in particular in relation to the size of the area of the skin and relative to the pulse wave velocity. On evaluating the color, brightness and/or volume, relative changes of less than 5% or even less than 1%, for example based on image data recorded by a digital video hardware usually applied in smartphones, can be taken into account in order to analyze the pulse wave passing through. Signal fluctuations, e.g. due to changing ambient light or changing temperatures, remain without any influence and can be filtrated by way of appropriate algorithms.

A subdivision into tiles, with each tile covering for example 100-10,000 or more pixels, causes an averaging of color and brightness values and thus a reduction of image noise. If required, the tiles may also overlap each other partly. A rectangular grid of tiles turned out to be particularly practical, though other arrangements of tiles (e.g. concentric, circular or spirally) are in principle conceivable. The tiles may be square, rectangular, circular, polygonal or have a different geometrical shape.

With a preferred embodiment, at least one biometrical feature is identified in the image data, with the positions of the tiles in relation to the at least one biometrical feature being equal in the sequence of image data. In this manner, it is made sure that always the same image area is evaluated, so that the covered modification profile of color, brightness and/or volume indeed reflects the pulse wave passing through rather than being adulterated by relative motions of the optical recording unit and the human body. The identification of biometrical features (e.g. identification of the position of eyes/mouth/nose/ears) in digital image data represents common practice. Reliably working algorithms which are well suitable for the inventive application do exist for this purpose. Likewise suitable is the identification of brighter and darker zones in the tissue which appear in the image sequence at reciprocating equal coordinates. Brighter and darker zones change their brightness and color during the inflowing pulse wave. However, relative to each other, these zones are stationary in the tissue and thus they may serve as reference for alignment of the tiles. In this manner, an area of the skin defined for the evaluation is pursued according to the invention when a body part is moved relative to the recording unit.

Furthermore, the tiling bears importance in order to achieve the required temporal resolution in the analysis of the pulse wave. Usual video hardware, e.g. in smartphones, furnishes an image rate of 20-50 images per second, which corresponds to a time resolution of 50-20 ms. This is usually insufficient for the purpose of determining vital parameters. By determining the modification profile of color, brightness and/or volume of several tiles located at different positions in the image, the effective temporal resolution can be increased beyond the resolution afforded by the video hardware, because the pulse wave passes at different moments of time (i.e. quasi with a different phase) through the positions of the different tiles. According to the present invention, the changes in color, brightness and/or volume values captured at different tile positions can be combined with each other in order to determine the modification profile and thus the pulse wave, with a temporal resolution that in comparison to the image rate of the video hardware is substantially higher. For example, if the area passed through by the pulse wave within 100 ms is subdivided into 100 tiles in the direction of transit, it results an effective temporal resolution of up to 1 ms. This is sufficient for a temporally very precise analysis of the pulse wave transit time and vital parameters associated therewith (RR-interval, pulse variability, etc.). In other words, according to the invention, a combined temporal/spatial evaluation of image values (brightness, color and/or volume) is performed in order to allow for an analysis of the pulse wave with the simplest video hardware (e.g. a smartphone) that has an adequate temporal resolution for diagnostic purposes.

In another advantageous embodiment of the present invention, the recording unit records stereo image data. This can be accomplished, for example, by using a second lens of a camera. These stereo image data then allow for a three-dimensional modelling of the area of the skin and for determining the volume, for example of the tiles. Exactness in determining the R-wave of a pulse wave passing through can thereby be increased substantially.

A particularly advantageous embodiment of the present invention provides for exposing the area of the skin by means of an illumination unit, in particular within a certain spectral range, to record the sequence of individual image data. Illumination of the area of the skin can thus be improved, for example if the ambient light is insufficient for recording image data in an adequately high quality. Moreover, the skin can be exposed with light in a certain spectral range, for example infrared or ultraviolet, in order to be able to better record changes in color or brightness of the skin. Furthermore, the spectral range can be adapted to the vital parameter to be determined. For example, for determining blood sugar, light can be used in the active spectral range of glucose whereby the measuring accuracy is increased.

In another embodiment, the sequence of individual image data is recorded by means of the recording unit spaced from the area of the skin. Thus, vital parameters can also be determined remotely. In particular with applications in which the person is in motion, as for example in sports, the vital parameter can also be determined without the person being in a direct contact with the device.

In another embodiment, the sequence of individual image data is recorded by means of the recording unit in direct contact with the area of the skin. Thus it is ensured that the sequence of image data is always recorded from exactly the same area.

In another embodiment, the sequence of individual image data is recorded by means of the recording unit via a pressure-exerting medium in contact with the area of the skin. The pressure-exerting medium can ensure a fixed distance between the skin and the recording unit, and on the other hand, the pressure-exerting medium can exert pressure on the skin. Exerting pressure on the skin influences blood flow and thus it is possible to improve the accuracy of the measurement.

The pressure-exerting medium may in particular be of a transparent configuration in order not to influence the recording of image data. Furthermore, the pressure-exerting medium may be arranged in annular shape around the recording unit, in particular around a lens of the recording unit. In this embodiment, the pressure-exerting medium can exert pressure on the skin while it does not impede the recording of image data.

In another embodiment, the motion data of a human body are recorded by means of at least one acceleration sensor. Accordingly, the motion data allow for reconstructing the physical stress of a person, which is taken into account when evaluating the image data and determining the pulse wave transit time. The acceleration sensor may also be provided in the device.

In another particularly advantageous embodiment, audio data are recorded by means of a microphone and allocated to the sequence of individual image data. From the audio data, it is possible to gain additional information for determining vital parameters. Thus, the sound of a pulse wave passing through can be taken into account for determining the pulse.

In an advantageous embodiment of the present invention, the recorded image data, acceleration data, and audio data are marked with a time stamp and saved on a memory unit of the device together with the time stamp for long-term evaluation. A long-term evaluation of vital parameters can thereby be accomplished. Saved image data, acceleration data, and audio data can then be read-out and evaluated by medical staff, for example after some hours or days. Accordingly, data and information can be transmitted via a data link of the device to a central host.

In particular, according to the method, it is possible to determine blood pressure and/or pulse. Pulse, i.e. heart frequency, indicates how frequently the heart contracts within a minute. Heart frequency at rest and under stress is the most commonly applied variable for assessing performance efficiency. For the heart frequency, limit values in different age brackets are described. However, individual differences are very substantial, because heart frequency is influenced by numerous factors. Apart from the chronological age, this includes training state, current health state, and the impact of numerous medicaments. Accordingly, a continuous heart frequency measurement implies the possibility of investigating health issues more closely. Heart frequency is a central parameter in training control and performance diagnostics.

Furthermore, oxygen saturation of the blood of a human body can be determined. Oxygen saturation indicates how many percent of the entire haemoglobin in the blood is loaded with oxygen. Among others, it allows for making statements on the effectiveness of oxygen transportation, that means primarily on the respiration. In accordance with the present invention, oxygen saturation is determined photometrically based on recorded image data in an actually known manner.

In combination with an analysis of the inventively acquired pulse wave curve, oxygen saturation can give conclusions as to the so-called cardiac output (heart minute volume). A suitable algorithm is known, for instance, under the designation PiCCO ("Pulse Contour Continuous Cardiac Output"). The heart minute volume (HMV) or heart time volume (HTV) is the volume of blood that is pumped in one minute by the heart via the aorta ascendingly in the blood circulation. Hence, the heart minute volume is a measure for the pump function of the heart and thus a very meaningful parameter, particularly in the field of cardiology. In the English language and also as a technical term in the German language, the term Cardiac Output (briefly CO) is utilized.

Moreover, pulse wave variability can be determined. Heart frequency variability results from pulse wave variability. It designates the potential of a human body to change the intervals between two heartbeats. The intervals are defined via the ventricular systole of the heart. In an electrocardiogram (ECG), the ventricular systole is designated as an R-indent, which is why one talks of an RR-interval in this regard. This RR-interval changes spontaneously even at rest, i.e. the distances between heart contractions differ from each other. With healthy persons, the heart action is started via a cycle generator. The center of excitation in the heart is called sine-atrial node. It is controlled by the autonomic nervous system and thus it is not subjected to the deliberate influence, but to the activity of the sympathetic nervous system. Physical but also psychic stresses are associated with an increase in the activity of the sympathetic trunk, and this leads to a rise in heart frequency. The parasympathetic nervous system, which is the antagonist to the sympathetic trunk in the autonomic nervous system, however, reduces heart frequency. It becomes evident that exterior influences (motion, thoughts), but also mechanical sequences (e.g. respiration) may influence the heart frequency. Since heart frequency variability has its origin in the center of the autonomic nervous system, the values measured allow for drawing conclusions as to diseases of the organic system. Probably, heart frequency variability is even more informative and meaningful than heart frequency for early identification of physiologic and pathological changes in the cardiovascular system. It is possible to observe and evaluate changes at rest and after athletic stresses. The following parameters may be of interest:

NN50=number of continuous RR-intervals ≥50 ms;
SDNN=standard deviation of all measured RR-intervals with a sinus rhythm;
rMSSD=root of the average value of squared differences of continuous RR-intervals In sport, the stress of an athlete and possible overtraining situations can be determined with the heart frequency variability. A well-aimed training control is enabled by the heart frequency variability. However, heart frequency variability is also applied in the medical field. The parameters of heart frequency variability change not only by athletic activity, but also due to the presence of risk factors and a reduction of these risk factors. For example, for diabetics with an existing neuropathy, time-related variables such as SDNN, NN50 and rMSSD are reduced.

Furthermore, consumption of narcotics (drugs), alcohol can be detected by way of the heart frequency variability. Various diseases take a characteristic influence on heart frequency variability. Finally, a person's fatigue can be detected by way of heart frequency variability.

Thus, it results an advantageous field of application for the inventive method for monitoring drivers of motor vehicles or machine operators. The optical recording unit can be solidly mounted in a motor vehicle or at a workplace, e.g. to generate a warning signal as soon as fatigue or any other condition of a driver and/or machine operator which might jeopardize security is identified on the basis of a certain vital parameter or certain vital parameters. Typically a warning signal is generated if one or more of certain vital parameters exceed or fall below a defined limit value.

Finally, blood sugar can also be determined in accordance with the present invention.

For blood sugar measurement, preferably an ear or a finger is recorded. The following can be utilized: absorption, that means the intake of energy through glucose molecules in and under the skin from irradiated infrared which leads to characteristic signals in the absorption spectrum. Furthermore, dispersion can be measured. Irradiated light is scattered, and from the type of scattering, the glucose content can be determined. Polarization can also be applied. Polarized light has a vibration plane which is turned by glucose (optical activity), and accordingly the glucose content results from the change of angles.

Another procedure is the percutaneous measurement by the aid of a broadband laser in the medium infrared range. According to this procedure, absorption of laser light is measured through glucose molecules existing in the blood, and in particular the absorption maximum of glucose in a wavelength range of 925 nm 5 or beyond can be utilized for this purpose. Other approaches are the measurement of the blood glucose level by way of fluorescent nanoparticles and the determination of the glucose content in lacrimal fluid.

In another preferred embodiment of the present invention, the determination of vital parameters comprises the determination of a breathing frequency. The pulse wave covered according to the invention is superimposed by oscillation with a frequency that is lower as compared to that of the pulse, i.e. the breathing frequency. In accordance with the present invention, this superimposed oscillation can be evaluated for determining the breathing frequency. If further parameters are integrated, it is in principle also possible to analyze the breath volume by way of recorded image data.

The present invention allows for realizing application programs (e.g. so-called "apps" for smartphones, inventively utilizing the integrated video hardware of a smartphone as an optical recording unit) for a so-called bio-feedback. Accordingly, at least one of the continuously measured vital parameters is appropriately visualized in real time, and the user practices the active control of the relevant vital parameter(s). Preferably, the user receives an optical or acoustic feedback indicating whether and to what extent the relevant vital parameter(s) lie(s) within a design value range or is brought by the user's control into the design value range. For example, a bio-feedback can be utilized for breathing regulation. By way of a visual representation of pulse wave and breathing curves on the display of a smartphone, it becomes possible to control both parameters. Through bio-feedback training, a user can realize the correlation between respiration and heart frequency, and learn how to regulate heart frequency via respiration. Hereof, it results an approach for exerting a positive influence on the central nervous system. What is trained and practiced is the so-called heart coherence. Likewise, a bio-feedback can be utilized to regulate heart frequency variability. A healthy heart in relaxed state distinguishes itself by a high heart frequency variability. It means the higher the state of relaxation, the higher the variability of heart frequency. By way of visually displaying the currently measured heart frequency variability, the degree of relaxation of one's own becomes visible to a user. On executing relaxation procedures, a user thus obtains direct feedback information on the efficiency of his/her relaxation technique.

Recording of image data can be executed in particular in the area of a human body's face, forehead, hand, finger, palm, ankle, or groin.

The present invention further relates to a device, in particular a smart device, for determining vital parameters of a human body, said device comprising at least:
　　an optical recording unit suitable for recording a sequence of individual image data of a limited area of the skin of a human body; and
　　a computing unit, set-up for evaluating the image data, comprising a determination of a pulse wave transit time and set-up for determination of vital parameters of a human body from the image data.

The present invention further relates to a method for authenticating a person by means of a device, in particular a smart device, comprising at least one optical recording unit, one computing unit, and one memory unit, comprising the following steps:
　　recording a sequence of individual image data of a human body's area of the skin, in particular of the face, by means of the optical recording unit;
　　evaluating the image data, comprising recognition of a pulse wave transit time by means of the computing unit;
　　comparing the image data with the profiles saved on the memory unit; and
　　issuing an authentication if image data match a saved profile.

Accordingly, it is possible, for example, to utilize profiles that reflect the blood value which is characteristic of each person. This can be done, for example, for a face. To this end, measurements of vital parameters are taken in advance from a group of persons, and the relevant profiles are established. When a person out of this group accedes to the device for authentication, it can be positively identified. Accordingly, no authentication is issued for a person that does not belong to this group.

In other words, authentication in accordance with the present invention is accomplished through brighter and darker zones existing in the tissue and appearing brighter or darker at reciprocating coordinates due to the pulse wave rushing through. These differences in color and/or brightness occur through the pulse waves in arterial blood vessels. Their evaluation may furnish data on the vital state of a person to be examined. Inanimate bodies, like imprints or copies intended for manipulating the examination are identified. The evaluation itself can be done with each pixel in the image. Bright and dark zones change their brightness and color during the pulse wave flowing in. Relative to each other, these zones are stationary in the tissue. Only by way of changed blood-oxygen portions are the changes in brightness and color generated in the tissue during the RR-interval. Upon expiry of an interval, these differences in brightness and color reverse back to the initial status. It remains this way until the next pulse wave. An area of the skin defined for evaluation is pursued on a motion of the body part. With each image obtained, from the video or individual image, the evaluation is subsequently performed based on the maximal brightness values as compared to previous images.

Hence, the present invention also relates to authenticating (or identifying) human beings, e.g. for securing mobile or immobile goods and property. Differentiated access controls are made possible by the inventive evaluation of images. An expensive authentication by way of chip cards or transponders is thus rendered superfluous. Required for authenticating are only images recorded of areas of a human being's body such as of the face or hand. For example, it takes aprox. 2 to 3 seconds to make the measurement with a 60 fps ("frames per second") camera in a smartphone. Manipulation is impossible with inanimate objects, because a pulse wave is verified.

The present invention also relates to a method for identifying a reaction of a person by means of a device, in particular a smart device, comprising at least one optical recording unit, one computing unit, and one memory unit, comprising the following steps:

recording a sequence of individual image data of a human body's area of the skin, in particular of the face, by means of the optical recording unit;

evaluating the image data, comprising recognition of a pulse wave transit time by means of the computing unit;

comparing the image data with the profiles saved on the memory unit; and issuing an authentication if image data match a saved profile.

The reaction patterns in particular describe the reaction of the blood flow to exterior influences. Accordingly, it is in particular possible to identify the reaction of a person's false statement. To this end, the reaction patterns are saved in advance, for example as a significant increase of the pulse to a person's false statement. When determining vital parameters, with comparing the reaction patterns, it can be ascertained whether a person, for example, has made a false statement.

The invention thus allows for determining vital parameters for different applications in a simple and cost-effective manner. Thus, vital parameters become easily accessible and can be utilized as a basis for a plurality of applications.

For the field of telemedical and medical applications, games, sport and leisure possibilities, online games, control of performance features on equipment, machinery, plant and vehicles, the present invention can provide the personal vital data.

Further features, details and advantages of the present invention result from the tenor of the patent claims as well as from the description of practical examples based on relevant illustrative figures.

BRIEF DESCRIPTION OF THE DRAWINGS

The present invention is now explained in further details by way of the subsequent text with reference to preferred practical examples based on illustrative figures, wherein.

The reference numbers and their meaning are summarized in the List of Reference Numbers. In general, equal reference numbers designate equal parts.

DETAILED DESCRIPTION OF THE PREFERRED EMBODIMENTS

Figure 1:
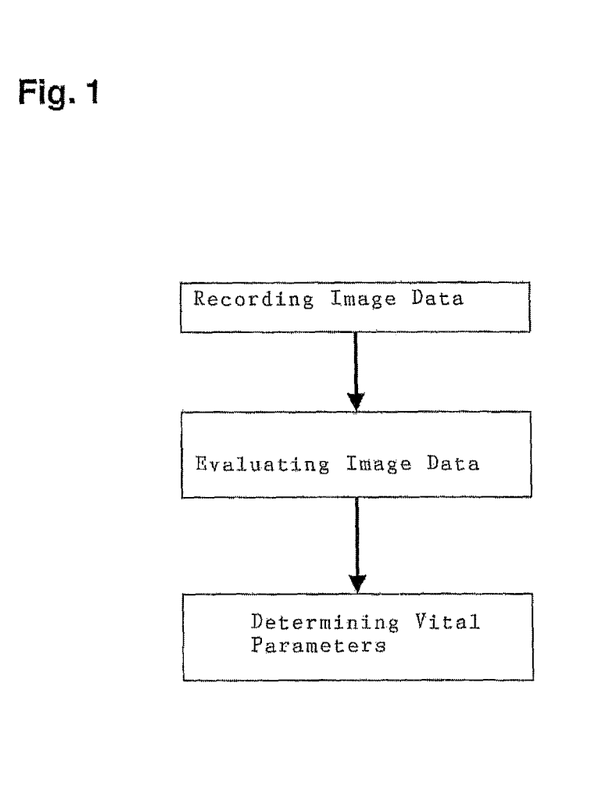
FIG. 1 is a schematic representation of method steps for determining vital parameters.

FIG. 1 shows a schematic representation of method steps, comprising a recording of a sequence of individual image data 20 of a single limited area of the skin 30 of a human body by means of an optical recording unit 11; evaluating the image data including a determination of a pulse wave transit time; and the determination of vital parameters of a human body from the image data by means of a computing unit 12.

Accordingly, the image data are recorded only from an area of skin 30. For example, this area may be a human's body face, parts of the face, such as forehead, a hand, parts of a hand, such as fingers, finger tip, palm, an ankle or the groin. In principle, every area of the skin can be utilized, though measuring accuracy of the vital parameter is increased with a high blood flow rate.

Image data are subsequently evaluated, and a pulse wave transit time is determined. This can be done a few days after recording, for example with a long-term measurement of a vital parameter. Accordingly, the image data are intermediately saved in a memory unit 13 until the evaluation of the image data is accomplished.

On determining vital parameters such as blood pressure, pulse, oxygen saturation of blood, pulse wave variability, or blood glucose, the pulse wave transit time is taken as the basis and evaluated in accordance with known procedures.

Figure 2:
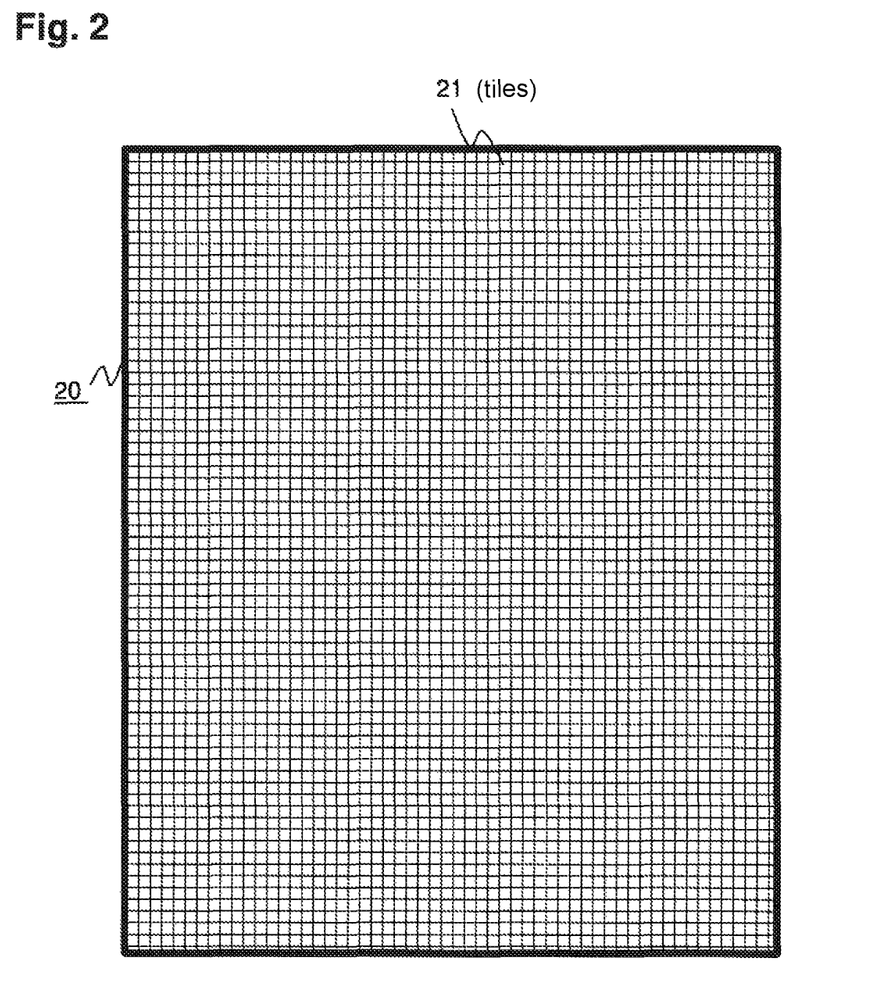
FIG. 2 is a schematic representation of a tiling of an individual image.

FIG. 2 shows a preferred embodiment for determining the pulse wave transit time. Accordingly, each individual image 20 is subdivided into a plurality of tiles 21, resulting in a grid of tiles 21. Color, brightness and/or volume are determined for each tile 21 of the individual image 20.

Volume is preferably determined from stereo-image data. In other words, a 3D camera having 2 camera lenses, preferably in a smart phone, can record images with a clearly defined distance at the same time. Evaluating the 3D camera is performed by applying the same principle as applied with one camera only. Accuracy, however, is by a multiple higher because more images are available for evaluation. Likewise, the defined distance from each other is beneficial to image evaluation. Smartphones with two separate cameras allow for extracting more precise data of the pulse wave from the image data.

A sequence of color, brightness, or volume of each tile 21 is thus obtained with the sequence of image data. The individual images 20 of the sequence are subsequently compared with each other in order to identify an alteration in color, brightness and/or volume in the sequence of image data. And then a modification profile, that means a temporal sequence of modifications, is established from the modifications in color, brightness and/or volume of tiles 21. Thereby, one can determine the pulse wave and its transit through the area of the skin. The image evaluation can be utilized for determining the distance covered by a pulse wave within a certain time. The pulse wave transit time is then determined from this modification profile. Assumptions on the size of the area of the skin can be taken as the basis.

For example, all recorded images are subdivided into tiles 21 as described hereinabove. Images recorded contain noise, inter alia because of motions while recording. For example, from 10 images obtained per second, assuming a pulse of 60 beats per minute, it results 10,000 tiles per original image with a tiling of 100×100 tiles 21. The original image shows a time extract of approx. 100 ms (10 images per second). By way of the 100×100 tiling grid, the overall image showing an extract of 100 ms is divided into 100 longitudinal parts. This corresponds to an effective temporal resolution of 1 ms (with a pulse rate of 60). This allows for an informative and convincing evaluation of the profile of the pulse wave when determining the pulse wave transit time.

As a result of the image analysis, the pulse wave transit time and the RR interval are determined. To determine the pulse wave way distance covered within a measured time, the smartphone images provided are tiles as described above and subsequently defined as images with value data on color, brightness and/or volume. Changes of these values, generated by pulsating waves of blood rich in oxygen, can now be determined from the image. Owing to the change in color, differences of values occur in the images of the recorded sequence which in a further computation can be evaluated as differences, for example in percent, length, height or even in color and brightness definitions. For example, the blood pressure can be computed from the pulse wave transit time.

Figure 3:
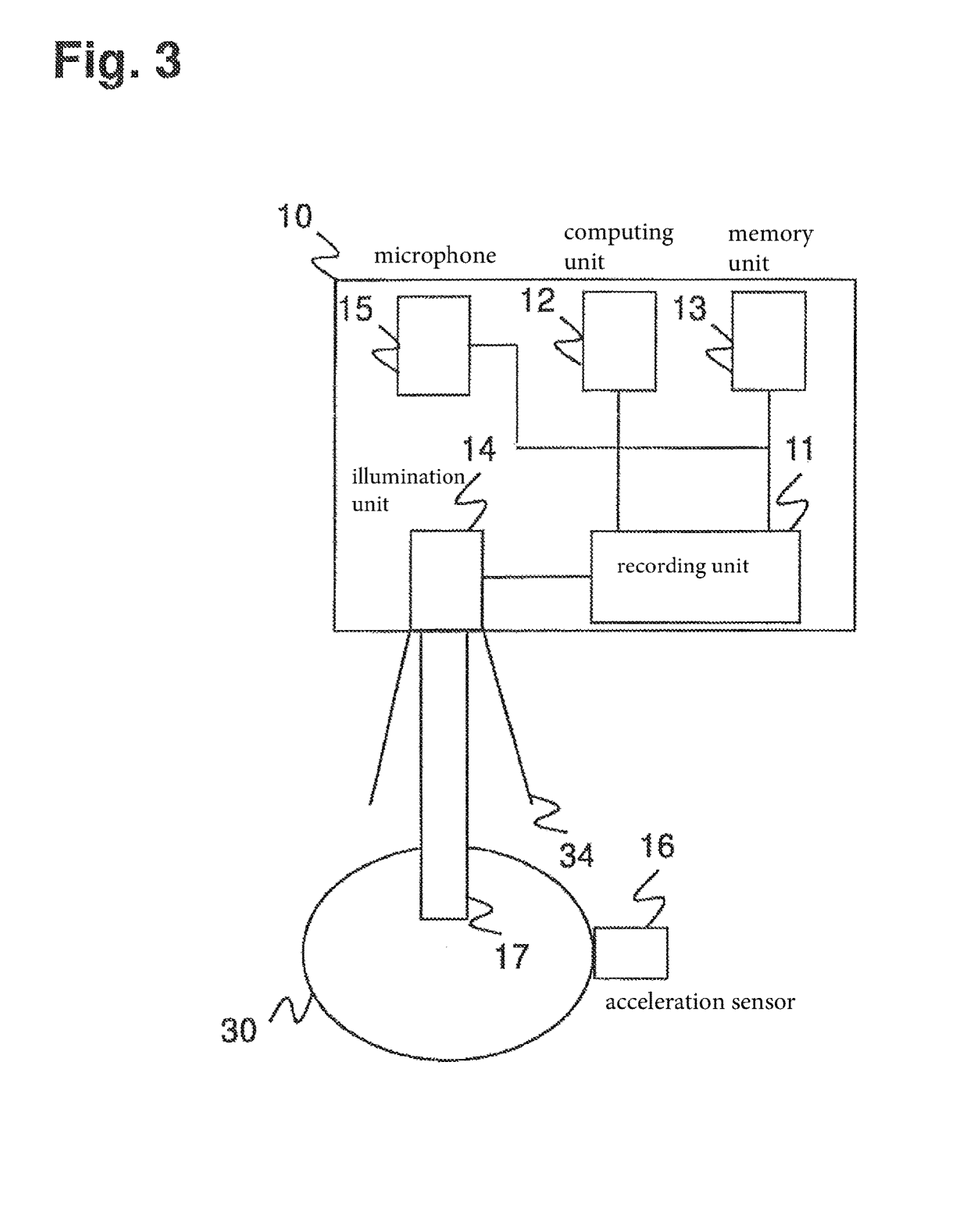
FIG. 3 is a schematic representation of a device for determining vital parameters.

FIG. 3 shows a device 10 comprised of a recording unit 11 for recording a sequence of individual images of a single limited area of the skin 30 of a human body, and a computing unit 12 for evaluating the image data, including determining a pulse wave transit time, and for determining vital parameters of a human body from the image data. The device 10 further comprises a memory unit 13 that can save image data for subsequent evaluation. Furthermore, an illumination unit 14 is provided for exposing the area of the skin 30. Light 34 from the illumination unit 14 in particular may have a certain spectral range. In the embodiment shown, the device is also equipped with a microphone 15 for recording audio data. The area of the skin 30 is furthermore provided with an acceleration sensor 16 for recording of motion data.

Further applications and practical examples of the present invention are explained in greater detail in other words in the following.

For magisterial and sovereign tasks, the data may also furnish decisive evidence for detection of criminal offences. A more efficient aid and identification in rescue tasks of injured persons is also possible. Surveillance cameras with a high resolution identify and authenticate persons.

Motion and vital data also provide information on a person's energy consumption in real time. A computation of a person's energy consumption in a temporally manageable action, by taking recourse to situations in the past and presence as well as environmental data, is furnished.

To illustrate holistic data of users, e.g. a patient's file, or the data from medical facilities, medical routine work, on the smallest screen, a search mode (e.g. in a visualized fractal) in the entire medical field is expedient and purposive.

Furthermore, an evaluation of a personal energy budget as well as its calculation to an imminent and potential performance requirement can be accomplished. For limit-value securing in sport with patients with defined indications, the measurement of blood pressure and pulse, breathing and oxygen saturation by the aid of pulse wave transit time measurement and RR interval, particularly in outdoor areas, constitutes an improvement. For example, the measurement is taken with a smartphone or an external camera. In case of conspicuous difficulties and a special presetting of the system, the smartphone can automatically call for help or offer direct proposals for training control.

Owing to its construction size and low demand for energy, data acquisition in water is also feasible. Placing the required components waterproof on the skin and measuring the blood pressure and pulse by means of the pulse wave transit time in water makes sense, not only from the viewpoint of therapeutical and sport therapeutical work. The non-contact measurement accomplishes the measurement of vital data in water by means of video and/or individual image evaluation even in a user's motion.

In leisure industry, for example with online games, or with gamer consoles, continuous vital data lead to more real games. An evaluation of a user's performance level becomes visible through pulse wave variability by evaluating the vital data from the image analysis.

Pulse wave variability decreases at growing age. At the same time, pulse wave variability drops and/or stagnates even under strong physical or psychic load on the organism. This point should also correlate with the transition to the anaerobic threshold. For training control, the individual anaerobic threshold (IAS) nowadays is often utilized as the basis for definition of training ranges. A threshold determination via heart frequency variability becomes easily possible by way of the present invention.

Performance efficiency in the anaerobic range is subject to a complex controlling process in the holistic contemplation of a human being. But it is also an indicator for exhaustion and can be verified in stored lactate. The threshold of heart frequency variability described by Berbalk and Neumann lies at approx. 2.4 mmol lactate and 10% under the performance rate at the IAS.

By way of a control of systems through personal vital data such as blood pressure and pulse, it is possible to equip leisure appliances, such as for example e-bikes, not only with an intelligent energy management. Incorporation of the motor, or actor, is effected via blood pressure and/or pulse values. Via the input of e.g. 60 Watts permanent performance rate of one's own, the motor power is adapted to the user's own shortage in performance rate by incorporating a motor depending on requirements, such as headwind or increased gradient of the terrain. The shortage of energy is offset. Thus, the user of a bike decreases his/her performance peaks. His/her degree of exhaustion is limited by the continuous discharge and his/her radius of action becomes greater with the e-bike. An equivalent result is achieved by timely changing the gears when using a bicycle. Near-real motion games, or even online training with several persons, at different locations, are utilized with one's own vital data for competitive games and sport activities.

A control based on determining vital parameters is conceivable, for example by identifying quicker breathing. This comprises, for instance:

control of emergency signals for persons and motor-driven vehicles on land, sea, and in the air;

control of performance features at motor-driven vehicles on land, sea, and in the air;

control of air conditioning in encapsulated appliances, building structures and objects with persons staying there inside, such as in ship building, for example in submarines, special structures, such as pressure vessels, as well as in aircraft and aerospace technology;

control of household appliances and energy management in domestic area, too, for example, a coffeemaker can turn itself on after its user has woken up or stood up;

control of heating, ventilation or electronic facilities at home is governed by the vital data and preset sequences;

control of firearms, e.g. to prevent triggering a projectile due to a pulse wave and/or an accruing pulse wave. This is applicable, for example, to biathletes who shoot in 200-300 ms within pulse waves.

LIST OF REFERENCE NUMBERS

10 Device
11 Recording unit
12 Computing unit
13 Memory unit
14 Illumination unit
15 Microphone
16 Acceleration sensor
20 Single image
21 Tile
30 Skin
34 Light

The invention claimed is:

1. A method for determining vital parameters of a human body via a device, in particular a smart device, said device comprising an optical recording unit and a computing unit, said method comprising the following steps:

recording a sequence of individual image data of limited area of the skin of the human body via the optical recording; unit;

evaluating the image data, including determining a pulse wave transit time by:
 subdividing into tiles the area of the skin reflected in the individual image data;
 determining a color, brightness and/or volume in each of the tiles of the individual image data;
 comparing the color, brightness and/or volume of the tiles in the consecutive image data of the sequence;
 determining a modification profile of the color, brightness and/or volume of a plurality of tiles located at different positions in the image and in accordance with the sequence of image data, wherein the modification profile reflects a pulse wave propagating through the area of the skin;
 temporally measuring a pulse wave velocity; and
 computing the pulse wave transit time from the modification profile and from the pulse wave velocity; and
determining one or more vital parameter(s) of the human body from the image data via the computing unit.

2. The method according to claim 1, wherein at least one biometric feature is recognized in the image data, with the positions of the tiles in relation to the at least one biometric feature being equivalent in the sequence of image data.

3. The method according to claim 1, wherein stereo image data are recorded via the recording unit.

4. The method according to claim 1, wherein for recording the sequence of individual image data the area of the skin is exposed via an illumination unit, in particular within a certain spectral range.

5. The method according to claim 1, wherein the sequence of individual image data is recorded via the optical recording unit at a space from the area of the skin.

6. The method according to claim 1, wherein the sequence of individual image data is recorded via the optical recording unit in direct contact with the area of the skin.

7. The method according to claim 1, wherein the sequence of individual image data is recorded via the optical recording unit via a pressure-exerting medium in contact with the area of the skin.

8. The method according to claim 1, wherein the motion data of the human body are recorded via at least one acceleration sensor.

9. The method according to claim 1, wherein audio data are recorded via a microphone and allocated to the sequence of the individual image data.

10. The method according to claim 1, wherein the recorded image data, acceleration data, and audio data are marked with a time stamp and saved together with the time stamp on a memory unit of the device for longterm evaluation.

11. The method according to claim 1, wherein the determination of vital parameters comprises the determination of blood pressure and/or pulse of a human body.

12. The method according to claim 1, wherein the determination of vital parameters comprises the determination of oxygen saturation of the blood of a human body.

13. The method according to claim 1, wherein the determination of vital parameters comprises the determination of a pulse wave variability.

14. The method according to claim 1, wherein the determination of vital parameters comprises the determination of a blood glucose value.

15. The method according to claim 1, wherein the determination of vital parameters comprises the determination of the rate of breathing.

16. The method according to claim 1, wherein the limited area of the skin for recording of image data is located in the area of a human body's face, forehead, hand, finger, palm, ankle, or inguen.

17. A device, in particular a smart device, for determining vital parameters of a human body, said device comprising at least:
 an optical recording unit, suitable for recording a sequence of individual image data of a limited area of the skin of a human body; and
 a computing unit set-up for evaluating the image data, the evaluating comprising determining a pulse wave transit time by: subdividing into tiles the area of the skin reflected in the individual image data, determining a color, brightness and/or volume in each of the tiles of the individual image data, comparing the color, brightness and/or volume of the tiles in the consecutive image data of the sequence, determining a modification profile of the color, brightness and/or volume of a plurality of tiles located at different positions in the image and in accordance with the sequence of image data, wherein the modification profile reflects a pulse wave propagating through the area of the skin, temporally measuring a pulse wave velocity, computing the pulse wave transit time from the modification profile and from the pulse wave velocity, the computing unit being set-up for determination of one or several vital parameter(s) of a human body from the image data.

18. The device according to claim 17, wherein the optical recording unit is configured as a three-dimensional recording unit for recording stereo-image data.

19. The device according to claim 17, wherein the device comprises an illumination unit for exposing the area of the skin, in particular with a certain spectral range.

20. The device according to claim 17, wherein the optical recording unit comprises a pressure-exerting medium for contacting the area of the skin.

21. The device according to claim 20, wherein the pressure-exerting medium is configured as a transparent medium.

22. The device according to claim 20, wherein the pressure-exerting medium is configured as a ring-shaped medium with a central opening.

23. The device according to claim 18, wherein a microphone is provided for recording audio data.

24. The device according to claim 17, wherein a motion sensor is provided for recording motion data.

25. The device according to claim 17, wherein a memory unit is provided for saving image data, audio data and/or motion data.

26. A method for authenticating a person via a device, in particular a smart device, the device comprising at least one optical recording unit, one computing unit, and a memory unit, the method comprising the following steps:
 recording a sequence of individual image data of a human body's area of the skin, in particular of the face, via the optical recording unit;
 evaluating the image data, comprising recognition of a pulse wave transit time via the computing unit via:
  subdividing into tiles the area of the skin reflected in the individual image data;
  determining a color, brightness and/or volume in each of the tiles of the individual image data;

comparing the color, brightness and/or volume of the tiles in the consecutive image data of the sequence;

determining a modification profile of the color, brightness and/or volume of a plurality of tiles located at different positions in the image and in accordance with the sequence of image data, wherein the modification profile reflects a pulse wave propagating through the area of the skin;

temporally measuring a pulse wave velocity; and computing the pulse wave transit time from the modification profile and from the pulse wave velocity;

comparing the image data with the profiles saved on the memory unit, the profiles reflecting the blood flow which is characteristic of each person; and issuing an authentication if image data match a saved profile.

27. A method for identifying a reaction of a person via a device, in particular a smart device, the device comprising at least an optical recording unit, a computing unit, and a memory unit, the method comprising the following steps:

recording a sequence of individual image data of an area of the skin of a human body, in particular of a face, via the optical recording unit;

evaluating the image data, including determining a pulse wave transit time by:

subdividing into tiles the area of the skin reflected in the individual image data;

determining a color, brightness and/or volume in each of the tiles of the individual image data;

comparing the color, brightness and/or volume of the tiles in the consecutive image data of the sequence;

determining a modification profile of the color, brightness and/or volume of a plurality of tiles located at different positions in the image and in accordance with the sequence of image data, wherein the modification profile reflects a pulse wave propagating through the area of the skin;

temporally measuring a pulse wave velocity; and computing the pulse wave transit time from the modification profile and from the pulse wave velocity;

comparing the image data with reaction patterns saved on the memory unit; and issuing a reaction if image data match a saved reaction pattern.

* * * * *

UNITED STATES PATENT AND TRADEMARK OFFICE
CERTIFICATE OF CORRECTION

PATENT NO. : 9,892,505 B2
APPLICATION NO. : 14/441917
DATED : February 13, 2018
INVENTOR(S) : Holger Redtel It is certified that error appears in the above-identified patent and that said Letters Patent is hereby corrected as shown below:

In the Claims

In Column 15, Line 3, (Line 7 of Claim 1) please delete the extra ";" from "recording; unit;" so that this line correctly reads: --recording unit;--.

Signed and Sealed this
Twenty-fourth Day of April, 2018

Andrei Iancu
*Director of the United States Patent and Trademark Office*